United States Patent [19]

Moore

[11] Patent Number: 4,461,717

[45] Date of Patent: Jul. 24, 1984

[54] STABLE GAS-CARRYING COMPOSITIONS

[75] Inventor: Robert E. Moore, Wilmington, Del.

[73] Assignee: Sun Tech, Inc., Philadelphia, Pa.

[21] Appl. No.: 360,039

[22] Filed: Mar. 19, 1982

[51] Int. Cl.$^3$ .................. A61K 31/025; B01J 13/00
[52] U.S. Cl. .................................. 252/312; 252/311; 252/314; 424/352
[58] Field of Search ............... 252/311, 312; 424/352

[56] References Cited

U.S. PATENT DOCUMENTS

| | | | |
|---|---|---|---|
| 3,547,995 | 12/1970 | Bartlett | 564/201 |
| 3,778,381 | 12/1973 | Rosano et al. | 252/311 |
| 3,823,091 | 7/1974 | Samejima et al. | 252/312 |
| 3,828,085 | 8/1974 | Price et al. | 260/404.5 |
| 3,911,138 | 10/1975 | Clark, Jr. | 424/352 |
| 3,962,439 | 6/1976 | Yokoyama et al. | 424/248 |
| 3,993,581 | 11/1976 | Yokoyama et al. | 252/312 |
| 4,041,086 | 8/1977 | Moore et al. | 570/130 |
| 4,105,798 | 8/1978 | Moore et al. | 424/352 |
| 4,220,606 | 9/1980 | Moore | 570/142 |

FOREIGN PATENT DOCUMENTS 55-147218 11/1980 Japan ..................... 252/312

OTHER PUBLICATIONS

Derwent Abstract J55147218–Describes Japanese Patent Publication 80/147218, Nov., 17, 1980 based on Japanese Appl'n. 80/46582 filed Apr. 9, 1980.

Dagani: "Synthetic Blood Research Progressing", Chemical and Engineering News, May 3, 1982, pp. 31–33.

*Primary Examiner*—Richard D. Lovering
*Attorney, Agent, or Firm*—J. Edward Hess; Donald R. Johnson; Patrick C. Baker

[57] ABSTRACT

Aqueous dispersions of a non-aromatizable perfluorinated $C_9$–$C_{18}$ polycyclic hydrocarbon having gas carrying properties, and a minor amount of an amidoamine oxide surfactant, the dispersions having at room temperature an average particle size of not over 0.1 micron initially and less than 0.3 micron for up to about one year or more. The ability of the dispersions to maintain low particle size over long periods at room temperature indicates exceptional stability, making them valuable as blood substitutes and therapeutic agents.

19 Claims, No Drawings

STABLE GAS-CARRYING COMPOSITIONS

BACKGROUND OF THE INVENTION

This invention relates to compositions having gas-transporting properties, and more particularly to aqueous dispersions of perfluoronated polycyclic hydrocarbons as the major gas-transporting agent and surfactants for dispersing the perfluorinated polycyclic hydrocarbon in the aqueous medium. The compositions maintain a range of very small particle size over long periods of time, of the order of 6 months to a year or more, and therefore provide the good stability required for use of the compositions as blood substitutes, organ perfusates and other uses wherein low particle size and stability for extensive periods is important.

A continuing problem in the search for compositions useful as blood substitutes or other applications based on gas-carrying properties, including transfer of oxygen, carbon dioxide and other gases, is stability of the composition. The leading candidate to date for synthetic blood applications is an aqueous emulsion of F-decalin and F-tripropylamine, as the gas-transporting ingredients, and as emulsifiers a combination of a polyoxyethylene-polyoxypropylene copolymer [commercially available as "Pluronic (trademark) F-68"] and a yolk phospholipid. While this composition is satisfactory with respect to gas-transfer capabilities, the components of the composition agglomerate and eventually separate unless the composition is frozen immediately after preparation and maintained in a frozen state until use. This requirement vastly limits applications and value of the composition since in many applications and environments the composition cannot be adequately maintained in a frozen state. Typical circumstances include emergency field use by the military.

Since small particle size of the gas transfer ingredients of the compositions is important in synthetic blood uses, stability must necessarily be defined in terms of maintenance of a low particle size range over the useful life of the composition, including storage time. While small particle size has been shown to be maintainable for extensive periods in the aforesaid compositions based on F-decalin, the utility of such compositions is drastically limited by the requirement that the compositions be maintained in a frozen state until use.

Typical of the literature describing synthetic blood compositions are the following U.S. Pat. Nos. 3,911,138 to L. C. Clark, Jr.; 4,105,798 to R. E. Moore and L. C. Clark, Jr.; 3,823,091 to Samejima et al; 3,962,439 to Yokoyama et al; 3,993,581 to Yokoyama et al; 3,828,085 to Price et al; and 3,778,381 to Rosano et al. None of the foregoing patents discloses or suggests gas transporting compositions for blood substitute, organ perfusate and therapeutic applications, wherein all of the requirements of an optimum blood substitute are exhibited, including high gas transfer capability, low retention time in the mammalian body, non-toxicity, low particle size range and, particularly, capability of being stored for extensive periods of time at room temperature without undue particle agglomeration or separation.

SUMMARY OF THE INVENTION

It has now been found that certain perfluorinated polycyclic hydrocarbons, known for their non-toxicity and high gas-carrying capabilities, can be effectively dispersed in aqueous media so as to provide uniform compositions which exhibit low particle size range over extensive periods of time at room temperature, thus demonstrating exceptional stability without need for freezing the compositions.

The compositions comprise stable, uniform, aqueous dispersions of a specific class of perfluorinated polycyclic hydrocarbons, containing as a dispersing aid an amidoamine oxide surfactant material. The compositions exhibit at room temperature ($25 \pm 2°$ C.) an average particle size initially, i.e. when made, of not over 0.15 micron, usually not over 0.10, e.g. 0.05 micron, and maintain a low particle size (less than 0.3 micron) for long periods, of the order of 35 weeks to a year or more, at room temperature.

DETAILED DESCRIPTION

The primary gas transporting ingredients of the composition are non-aromatizable, perfluorinated $C_9$–$C_{18}$ polycyclic hydrocarbons containing at least two bridgehead carbon atoms linked through a bridge containing at least 1 carbon atom. These gas transfer agents are fully described, together with synthesis, in the aforementioned U.S. Pat. No. 4,105,798 and in U.S. Pat. Nos. 3,641,167 and 4,041,086, both to R. E. Moore et al. Other methods of synthesis of the gas transfer reagents of the invention are described in U.S. Pat. No. 4,220,606 to R. E. Moore. The disclosures of these patents are incorporated herein by reference in their entireties. By way of summary but not limitation, the perfluorinated polycyclic hydrocarbons of the invention include non-aromatizable polycyclic perfluorocarbons preferably containing 9–12 carbon atoms and generally having not more than 4 rings, more usually 2–3 rings. By "non-aromatizable" is meant the compounds cannot be aromatized without destruction of the original carbon-to-carbon cyclic bonds. This distinguishes the perfluorocompounds of the invention from perfluoro multi-ring compounds such as perfluorodecalin and similar compounds.

Representative gas transfer components of the invention are the perfluoro derivatives of such $C_9$–$C_{18}$ polycyclic compounds as bicyclononanes (e.g. bicyclo[3.3.1]nonane, 2,6-dimethylbicyclo[3.3.1]nonane or 3-methylbicyclo[3.3.1]nonane), adamantane, methyl and dimethyladamantane, trimethyladamantane, ethyladamantane, tetrahydrodicyclopentadiene, methyl and dimethylbicyclooctanes, ethylmethyladamantanes, ethyldimethyladamantane, tetrahydrobinor-S, methyldiadamantane, triethyladamantane, trimethyldiadamantane, ethyldimethyldiadamantane, pinane, camphane, 1,4-6,9-dimethanoldecalin, bicyclo[4.3.2]undecane, trimethylbicyclo[3.3.1]nonane, and the like, including mixtures of any two or more thereof. Preferred compounds are F-1,3-dimethyladamantane, F-trimethylbicyclononane, and mixtures thereof, e.g., ranging from about 90/10 to 10/90 by weight.

The amidoamine oxide surfactants, found to be uniquely effective for providing the stable aqueous dispersions of the invention, are known materials as disclosed in U.S. Pat. Nos. 3,828,085 to Price et al and 3,547,995 to Bartlett. Certain species of the amidoamine oxide surfactants are also disclosed in U.S. Pat. No. 3,778,381 to Rosano et al. The disclosures of these patents are herein incorporated by reference in their entireties.

By way of summary but not limitation the amidoamine oxide surfactants may be used singly or in mixtures of two or more and may be described as follows:

$$R_fCON-RQ \quad (1)$$
$$\quad\quad | \quad\quad$$
$$\quad\quad Y \quad\quad$$

wherein $R_f$ is a perfluoroalkyl radical of 4 to about 25 carbon atoms or a polyfluoroalkoxyalkyl radical wherein the alkoxy group may contain 3 to about 40 carbon atoms of which at least a major portion thereof are perfluorinated and the alkyl group may contain 2 to about 40 carbon atoms, fluorinated or unfluorinated; Y is hydrogen or alkyl of 1 to 6 carbon atoms; R is an alkylene radical of the formula $$-C_zH_{2z}-$$

wherein z is an integer of 1 to 6; and Q is an aliphatic amine oxide radical of the formula:

$$\begin{array}{c} R_5 \\ | \\ -N-R_6 \\ \downarrow \\ O \end{array}$$

wherein $R_5$ and $R_6$ are each alkyl radicals of 1 to 6 carbon atoms or hydroxy-terminated alkyl radicals of 2 to 6 carbon atoms. In all cases the alkoxy, alkyl and alkylene groups may be straight or branched chain.

Preferred subclasses of the surfactants are those of the following formulas (2) and (3):

$$C_nF_{2n+1}O(CF_2)_x\overset{O}{\overset{\|}{C}}NH(CH_2)_y\overset{O}{\overset{\uparrow}{N}}R^1R^2 \quad (2)$$

wherein n is at least 3 (preferably 3-10), x is at least 2 (preferably 2-6), y is at least 1 (preferably 2-6), and $R^1$ and $R^2$ independently are alkyl radicals containing 1-6 carbon atoms.

$$C_nF_{2n+1}\overset{O}{\overset{\|}{C}}NH(CH_2)_z\overset{O}{\overset{\uparrow}{N}}R^1R^2 \quad (3)$$

wherein n is at least 3 (preferably 3-10), z is at least 1 (preferably 2-6), and $R^1$ and $R^2$ independently are alkyl radicals containing 1-6 carbon atoms.

Specific amidoamine oxides within the scope of the above formula are the products described in Examples 1-6 of U.S. Pat. No. 3,828,085, namely:

$$CF_3(CF_2)_6\overset{O}{\overset{\|}{C}}NH(CH_2)_3\overset{O}{\overset{\uparrow}{N}}(CH_3)_2$$

$$(CF_3)_2CFO(CF_2)_3\overset{O}{\overset{\|}{C}}NH(CH_2)_3\overset{O}{\overset{\uparrow}{N}}(CH_3)_2$$

$$(CF_3)_2CFO(CF_2)_5\overset{O}{\overset{\|}{C}}NH(CH_2)_3\overset{O}{\overset{\uparrow}{N}}(CH_3)_2$$

$$(CF_3)_2CFO(CF_2)_7\overset{O}{\overset{\|}{C}}NH(CH_2)_3\overset{O}{\overset{\uparrow}{N}}(CH_3)_2$$

$$(CF_3)_2CFO(CF_2)_5\overset{O}{\overset{\|}{C}}NH(CH_2)_3\overset{O}{\overset{\uparrow}{N}}(C_2H_5)_2$$

$$(CF_3)_2CFO(CF_2)_8(CH_2)_{10}\overset{O}{\overset{\|}{C}}NH(CH_2)_3\overset{O}{\overset{\uparrow}{N}}(C_2H_5)_2$$

The aqueous dispersions of the invention are prepared by any mixing technique which will provide a uniform blend of the ingredients. In one preparative technique the surfactant is mixed with the water under suitable agitation followed by introduction of the perfluorinated polycyclic hydrocarbon (hereinafter abbreviated to "perfluorocarbon" or "PFC"). Since the PFC is extremely hydrophobic, high energy mixing normally must be employed, such as homogenization or sonic energy. One such device is the "Sonicator" (trademark), Model 350, available from Heat-Systems Ultrasonics Inc. This device has a maximum power output of 350 watts controllable on settings of 1-10. Because the dispersion will rapidly heat up during blending in the "Sonicator", it is preferred to blend over several mixing cycles separated by cooling periods. After blending, the dispersion is filtered and transferred to suitable storage vessels. Preferably, the dispersions are kept under refrigeration, at a temperature of about 4° C., but the dispersions are effective for use as artificial blood compositions at room temperature.

The PFC and surfactant components may be blended into water in any proportions which will provide uniform dispersions. Typical proportions are about 5 to 50% of PFC based on the volume of the total composition and about 0.5 to 10% of the surfactant based on the total weight of the composition. Preferred proportions are about 10-30% by volume of the PFC and about 2-5% by weight of the surfactant.

A significant aspect of the invention is that at a given concentration of PFC and surfactant the viscosity is far less than that of the artificial blood emulsions containing F-decalin, F-tripropylamine and "Pluronic" type surfactants described above. For example, a 40% PFC dispersion of the invention is less viscous than a 20% by weight gas transfer emulsion of the F-decalin type. In addition the dispersions of our invention can carry more than twice as much oxygen or other gas as the F-decalin-Pluronic type emulsions at the same viscosity. When this feature is taken with the small particle size range, stability and non-toxicity of the dispersions, it will be seen that the compositions of the invention have unique and highly advantageous as artificial blood compositions or in other applications.

The dispersions of the invention have very small particle size and because of this often exhibit some properties of solutions, e.g., transparency. They contain, however, two phases, PFC and aqueous, as shown by electron microscopy.

As will be evident from the particle size data of the examples below, the compositions of the invention maintain a range of low particle size for long periods of time, and have a particle size of not more than 0.2 after 35 weeks at 25±2° C., and have an average particle size under 0.3 micron after 1 year under the same conditions.

In other words, a plot of particle size versus time yields a line of relatively small slope. This is far superior to other known blood compositions which, although they can be made in small particle sizes initially, increase in particle size much more quickly. As a result, a particle size-time plot gives a line of much steeper slope.

Another advantage of our compositions is that not only are the particle sizes low but the distribution of sizes is remarkably small. The average particle size reflects the average of the size of each individual particle in the dispersion but does not indicate, for example, if the average is made up of many very large particles and very small particles, in which case the average may appear satisfactory. This only appears if the distribution around the average is known.

The distribution range of our compositions around the average is very small. Initially 90–95% of the particles are 0.15 micron or less. After a period of 35 weeks to a year, over 90%, usually 95%, of the particles still are within the average ±0.1 micron.

It is apparent from the above that the compositions of the invention maintain excellent stability at or about room temperature for long periods, thus providing a uniquely effective gas transfer composition for use as a synthetic blood component or for other therapeutic applications.

In this connection, electron microscopy and laser light scattering spectrometry have provided a valuable service because they measure actual particle size. Mere visual inspection of the compositions, even over extended periods, cannot provide meaningful basis for determinations of efficacy because, even if no separation was observed over such period, one would not know whether or not the particle size was sufficiently low and was maintained in a sufficiently low range for such period so that the dispersions would be and would remain effective as artificial blood compositions.

Optical density measurements likewise are misleading when such measurements are compared to the same measurements on alternate compositions, including compositions based on other gas transfer agents and/or surfactants. Optical density measurements are valid only if made on single compositions since such measurements do not take into consideration the refractive indices of other components of a composition. Moreover, since the refractive index of the PFC component of the invention is close to that of water, optical density measurement would not adequately reflect the presence of the PFC. Accordingly, actual particle size determinations are the only valid means for adequately distinguishing one blood substitute composition from another with respect to stability.

All particle size references herein are weighted average by electron microscopy (EM) unless specified to be by laser spectrometry (LS). Both usually give essentially the same result and are thus equivalent, but electron microscopy is preferred because it also enables the user to determine the particle size distribution, whereas the laser technique normally does not. If the two techniques give different results a correlation is easily developed to apply to the LS results to convert them to the equivalent EM results. The LS data was obtained with a "Nicomp Laser Scattering Spectrometer", Model HN5-90, coupled with a "Computing Auto-Correlator", Model 6864, both available from Nicomp Instruments, Santa Barbara, Ca. The EM data was obtained with a standard transmission electron microscope at Delaware Scientific, Bear, Del.

The compositions of the invention may be used as artificial blood materials on organ perfusates according to the procedures set forth in U.S. Pat. No. 3,911,138 and other literature on the subject. The following examples further illustrate the invention.

EXAMPLE 1

A surfactant solution was prepared by dispersing in water a sufficient amount of the following amidoamine oxide (Surfactant A) to provide a 2% by weight solution:

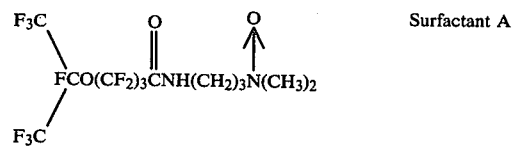

Surfactant A

To the sonication chamber of a "Sonicator" (trademark) mixing device (Heat-Systems Ultrasonics, Inc., Model 350) was added 27 cc of the 2% surfactant solution, followed by slow addition (over 3–4 minutes) under low sonification power of 3 cc of a PFC composition consisting of an about 50/50 by weight liquid mixture of F-1,3-dimethyladamantane and F-trimethylbicyclo[3.3.1]nonane, to provide a total of 30 cc of composition. (The PFC mixture was previously saturated with $CO_2$ to inhibit formation of fluoride ions). The sonification horn was then turned up to full power (setting of 10 on a scale of 1–10) for one minute followed by a cooling period. This cycle was repeated about 15 times or until such time as uniform dispersion was obtained.

The dispersion was then filtered through a 0.22 micron "Millipore" (trademark) filter and divided into two portions. The first portion was refrigerated at 4° C. The second portion was kept at room temperature (25±2° C.). Both portions were transparent.

EXAMPLE 2

Essentially as described in Example 1, refrigerated (4° C.) portions and room temperature portions (RT) of an aqueous dispersion were prepared, the only compositional difference being substitution of the following surfactant (Surfactant B) for the surfactant of the dispersion of Example 1:

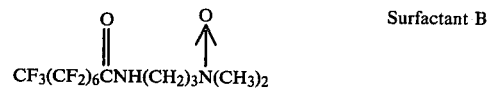

Surfactant B

EXAMPLE 3

Essentially as described in Example 1, refrigerated (4° C.) portions and room temperature portions (RT) of an aqueous dispersion were prepared, the only compositional difference being substitution of the following surfactant (Surfactant C) for the surfactant of the dispersion of Example 1:

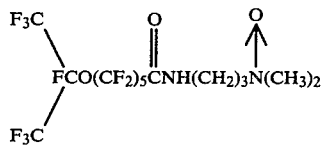

EXAMPLE 4

Other aqueous dispersions were prepared using the surfactants and an essentially equivalent blending process as described in Examples 1–3 but substituting different perfluorocarbon gas transfer components. In each case the dispersions contained 10% by volume of the gas transfer ingredient and 2% by weight of surfactant. The particle sizes of the dispersions were then determined with the results set forth in the following tables.

In the tables the fluorocarbon gas transfer agents are identified as follows:

PFC-Inv.: perfluorocarbon of the invention, as in Examples 1–3: F-dimethyladamantane/F-trimethylbicyclononane (50/50)
F-Dec: F-decalin
F-DMCHMA: F-N,N-dimethylcyclohexylmethylamine (another known blood substitute)
F-TPA: F-tripropylamine The particle size determinations were by elctron microscopy (EM) and/or laser light scatter spectrometry (LS) and particle sizes are reported for refrigerated (4° C.) and room temperature portions (RT: 25±2° C.). "EB" indicates that the emulsion broke. The asterisk (*) indicates agglomerates. Those dispersions of both F-decalin and F-TPA contained these fluorocarbons in a 7:3 ratio by weight.

Table I shows that dispersions containing the select class of perfluorocarbon gas transfer agents (PFC) of the invention and an amidoamine oxide surfactant maintained average particle sizes below 0.15 micron for the duration of the test, while dispersions containing the same surfactants but different fluorocarbon gas transfer agents agglomerated, broke or exhibited larger average particle sizes.

TABLE I
Stability of Fluorocarbon Dispersions
Time (Weeks)
Average Particle Sizes (Micron)

Surfactant A

|  | Anal. | 1 | 6 | 9 | 19 | 25 | 30 | 35 |
|---|---|---|---|---|---|---|---|---|
| PFC-Inv., 4° C. | EM |  |  |  | .10 | .124 | .118 | .123 |
| PFC-Inv., RT | EM |  |  |  | .112 | .118 | .114 |  |
| F-Dec., 4° C. | LS | .19 | .32 | .37 |  | EB |  |  |
| F-Dec., RT | LS | .19 | .43 | .50 | EB |  |  |  |

Surfactant B

|  |  | 1 | 4 | 5 | 7 | 9 | 10 | 13 | 18 | 24 |
|---|---|---|---|---|---|---|---|---|---|---|
| PFC-Inv. | EM |  |  |  | .093 |  |  | .095 | .100 | .105 |
| PFC-Inv. | EM |  |  |  |  | .104 |  |  | .128 | .137 |
| F-Dec. 4° C. | LS | .13 | .225 | .26 |  |  |  |  |  |  |
| F-Dec., RT | LS | .13 | .29 | .32 |  |  |  |  |  |  |
| F-Dec/F-TPA, 4° C. | LS | .13 |  |  |  | .17 |  |  |  |  |
| F-Dec/F-TPA, RT | LS | .13 | .17 |  |  | .19 | .21 |  |  |  |
| F-DMCHMA, 4° C. | LS | .09 |  |  |  |  | .195 |  |  |  |
| F-DMCHMA, RT | LS | .09 | .18 |  | .23 | .26 |  |  |  |  |

Surfactant C.

|  | Anal. | 1 | 2 | 4 | 5 | 6 | 10 | 15 | 19 |
|---|---|---|---|---|---|---|---|---|---|
| PFC-Inv., 4° C. | EM |  |  |  |  | .07 | .097 | .13 | .12 |
| F-Dec., 4° C. | LS |  | .124 | .19 | .225 |  |  |  |  |
| F-Dec., RT | LS |  | .124 |  | .195 |  |  |  |  |
| F-Dec/F-TPA, 4° C. | LS |  | .13 | .13 |  | .19 |  |  |  |
| F-Dec/F-TPA, RT | LS |  | .13 |  | .15 |  |  |  |  |

I claim:

1. A gas transporting composition comprising a stable, uniform, aqueous dispersion of a non-aromatizable perfluorinated $C_9$–$C_{18}$ polycyclic hydrocarbon containing at least two bridgehead carbon atoms linked through a bridge containing at least one carbon, atom, said dispersion containing an effective for dispersion of the perfluorinated hydrocarbon, of an amidoamine oxide surfactant of the formula

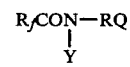

wherein $R_f$ is a perfluoroalkyl radical of 4 to about 25 carbon atoms or a polyfluoroalkoxyalkyl radical wherein the alkoxy group contains 3 to about 40 carbon atoms of which at least a major portion thereof are perfluorinated and the alkyl group contains 2 to about 40 carbon atoms, fluorinated or unfluorinated; Y is hydrogen or alkyl of 1 to 6 carbon atoms; R is a straight- or branched-chain alkylene radical of the formula

wherein z is an integer of 1 to 6; and Q is an aliphatic amine oxide radical of the formula:

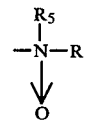

wherein $R_5$ and $R_6$ are each alkyl radicals of 1 to 6 carbon atoms or hydroxy-terminated alkyl radicals of 2 to 6 carbon atoms; said composition exhibiting at 25±2°

C. an average particle size of not over 0.1 micron initially and less than 0.3 micron after about one year.

2. The composition of claim 1 wherein said average particle size is less than 0.15 micron after 35 weeks.

3. The composition of claim 1 wherein said average particle size is not over about 0.2 micron after one year.

4. The composition of claim 1 wherein a predominant portion of the particles have a particle size less than 0.1 micron after 35 weeks.

5. The composition of claim 1 wherein the perfluorinated polycyclic hydrocarbon comprises about 5 to 50% by volume of the composition, and the surfactant comprises about 0.5 to 10% by weight of the composition.

6. The composition of claim 1 wherein the surfactant is

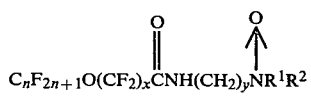

wherein n is at least 3, x is at least 1, y is 1–6, and $R^1$ and $R^2$ independently are alkyl radicals containing 1–6 carbon atoms.

7. The composition of claim 1 wherein the surfactant is

wherein n is at least 3, z is 1–6, and $R^1$ and $R^2$ independently are alkyl radicals containing 1–6 carbon atoms.

8. The composition of claim 1 wherein the surfactant is

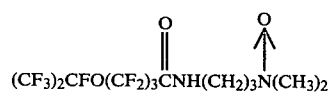

9. The composition of claim 1 wherein the surfactant is

10. The composition of claim 1 wherein the surfactant is

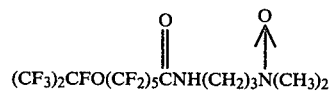

11. The composition of claim 1 wherein the perfluorinated polycyclic hydrocarbon is a perfluorinated adamantane.

12. The composition of claim 1 wherein the perfluorinated polycyclic hydrocarbon is a perfluorinated bicyclononane.

13. The composition of claim 1 wherein the perfluorinated polycyclic hydrocarbon is a mixture of a perfluorinated adamantane and a perfluorinated bicyclononane.

14. The composition of claim 1 wherein the perfluorinated polycyclic hydrocarbon is F-dimethyladamantane.

15. The composition of claim 1 wherein the perfluorinated polycyclic hydrocarbon is F-trimethylbicyclononane.

16. The composition of claim 1 wherein the perfluorinated polycyclic hydrocarbon is a mixture of F-dimethyladamantane and F-trimethylbicyclononane.

17. The composition of claim 1 wherein the surfactant is

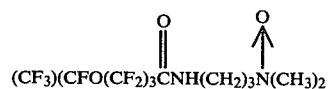

and the perfluorinated polycyclic hydrocarbon is a mixture of F-dimethyladamantane and F-trimethylbicyclononane.

18. The composition of claim 1 wherein the surfactant is

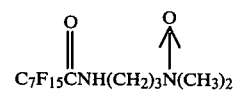

and the perfluorinated polycyclic hydrocarbon is a mixture of F-dimethyladamantane and F-trimethylbicyclononane.

19. The composition of claim 1 wherein the surfactant is

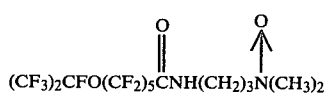

and the perfluorinated polycyclic hydrocarbon is a mixture of F-dimethyladamantane and F-trimethylbicyclononane.

* * * * *